United States Patent
Sherry et al.

(10) Patent No.: US 8,992,551 B2
(45) Date of Patent: Mar. 31, 2015

(54) COMPOSITE SURGICAL IMPLANTS FOR SOFT TISSUE REPAIR

(75) Inventors: John Sherry, Needham, MA (US); Timothy P. Harrah, Cambridge, MA (US); Jianmin Li, Lexington, MA (US); James Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 583 days.

(21) Appl. No.: 13/014,533

(22) Filed: Jan. 26, 2011

(65) Prior Publication Data
US 2011/0184228 A1    Jul. 28, 2011

Related U.S. Application Data

(60) Provisional application No. 61/299,080, filed on Jan. 28, 2010.

(51) Int. Cl.
*A61B 17/08* (2006.01)
*A61F 2/02* (2006.01)
*A61F 2/00* (2006.01)

(52) U.S. Cl.
CPC ....... *A61F 2/0045* (2013.01); *A61F 2002/0068* (2013.01)
USPC ........................................ 606/151; 623/23.72

(58) Field of Classification Search
CPC ................... A61F 2/0045; A61F 2002/0068
USPC .................. 606/151; 623/11.11, 23.72, 23.75, 623/23.76; 600/37
See application file for complete search history.

(56) References Cited

U.S. PATENT DOCUMENTS

| 4,585,458 A * | 4/1986 | Kurland ..................... 623/13.17 |
| 7,060,103 B2 * | 6/2006 | Carr et al. .................. 623/23.72 |
| 7,582,576 B2 * | 9/2009 | Snijder et al. ..................... 442/1 |
| 7,722,528 B2 * | 5/2010 | Arnal et al. ..................... 600/30 |
| 8,167,894 B2 * | 5/2012 | Miles et al. ..................... 606/139 |
| 2002/0038151 A1 * | 3/2002 | Plouhar et al. ............. 623/23.72 |
| 2003/0023316 A1 * | 1/2003 | Brown et al. ............... 623/23.72 |
| 2004/0010320 A1 * | 1/2004 | Huckle et al. .............. 623/23.72 |
| 2004/0059356 A1 | 3/2004 | Gingras |
| 2005/0101834 A1 * | 5/2005 | Merade .......................... 600/37 |
| 2005/0240281 A1 * | 10/2005 | Slivka et al. ............... 623/23.75 |
| 2006/0142786 A1 * | 6/2006 | Mathisen et al. ............ 606/151 |
| 2006/0173471 A1 * | 8/2006 | Carr et al. ..................... 606/151 |
| 2006/0205998 A1 | 9/2006 | Li |
| 2007/0248638 A1 * | 10/2007 | Van Dyke et al. ............ 424/422 |
| 2007/0282160 A1 | 12/2007 | Sheu et al. |

(Continued)

FOREIGN PATENT DOCUMENTS

EP    1520552 A1 *  4/2005
GB    1008193 A  * 10/1965

OTHER PUBLICATIONS

"AMS Systems with InteXe-n LP Porcine Dermal Matrix" 4 pages, © 2006 American Medical Systems, Inc.

(Continued)

*Primary Examiner* — Julian W Woo
*Assistant Examiner* — Lucas Paez
(74) *Attorney, Agent, or Firm* — Kacvinsky Daisak Bluni PLLC

(57) ABSTRACT

According to one aspect of the invention, composite implants for soft tissue repair are provided which comprise (a) a substantially two-dimensional piece of biologic matrix material and (b) one or more non-absorbable synthetic polymeric filaments.

15 Claims, 3 Drawing Sheets

(56) References Cited

U.S. PATENT DOCUMENTS

| | | | |
|---|---|---|---|
| 2008/0009667 | A1 | 1/2008 | Longhini |
| 2008/0147198 | A1* | 6/2008 | Cherok et al. .............. 623/23.72 |
| 2009/0036996 | A1* | 2/2009 | Roeber ....................... 623/23.72 |
| 2009/0152766 | A1* | 6/2009 | Rousseau et al. ............. 264/241 |
| 2009/0171377 | A1* | 7/2009 | Intoccia et al. ................ 606/151 |
| 2009/0276057 | A1* | 11/2009 | Trabucco et al. ........... 623/23.72 |
| 2009/0281558 | A1 | 11/2009 | Li |
| 2009/0281635 | A1 | 11/2009 | Li et al. |
| 2009/0318752 | A1 | 12/2009 | Evans |
| 2010/0016872 | A1* | 1/2010 | Bayon et al. ................... 606/151 |

OTHER PUBLICATIONS

Myung Jae Jeon et al., "Use of Grafts in Pelvic Reconstructive Surgery," Yonsei Medical Journal, vol. 48, No. 2, pp. 147-156, 2007.

Neeraj Kohli et al., "Use of Synthetic Mesh and Donor Grafts in Gynecologic Surgery," Curr. Womens Health Rep. Aug. 2001;1(1):53-60.

"Avaulta Plus® BioSynthetic Support System", Avaulta Plus® BioSynthetic Support System, 1 page. Downloaded Sep. 18, 2009 from http://www.bardurological.com/products.

Medcompare™, "Avaulta Plus™ BioSynthetic Support System—Bard Urological" 1 page. Downloaded Sep. 18, 2009 from http://www.medcompare.com.

Avaulta® BioSynthetic Support System, 4 pages, © 2005 C.R. Bard, Inc.

Stephen F. Badylak, et al., "Extracellular matrix as a biological scaffold material: Structure and function," Acta Biomaterialia 5 (2009) 1-13.

Lisa M. Pierce, et al., American Journal of Obstetrics & Gynecology, May 2009, 549.e8.

R. Mori, et al., The Journal of Experimental Medicine, vol. 205, No. 1, Jan. 21, 2008, pp. 43-51.

E.C. Trabuco, et al., Int Urogynecol J (2007) 18:555-563.

E.C. Trabuco, et al., American Journal of Obstetrics & Gynecology, Dec. 2007, 638.e1-638.e6.

Liang et al., Effects of crosslinking degree of an acellular biological tissue on its tissue regeneration pattern, Biomaterials 25 (2004) 3541-3552.

\* cited by examiner

COMPOSITE SURGICAL IMPLANTS FOR SOFT TISSUE REPAIR

RELATED APPLICATIONS

This application claims priority from U.S. provisional application 61/299,080, filed Jan. 28, 2010, which is incorporated by reference herein in its entirety.

FIELD OF THE INVENTION

The present invention relates to surgical implants for soft tissue repair.

BACKGROUND INFORMATION

Surgical implants have been used in a variety of soft tissue repair procedures and include, for example, biologic grafts and meshes used for pelvic floor repair, for hernia repair, for the treatment of stress urinary incontinence, for thoracic wall defect repair, for breast support, and for cosmetic and reconstructive surgery, among others.

Non-absorbable synthetic mesh materials (e.g., polypropylene, etc.) provide durable long-lasting soft tissue repairs. Such materials trigger a biologic foreign body response (FBR) when implanted, establishing chronic inflammation and FBR at the site of implantation. A typical FBR usually starts with a local inflammatory response, accumulation of monocytes and macrophages, followed by fibrinogen deposits, fibrosis and scar tissue formation. This fibrous connective scar tissue becomes integrated into the mesh or forms a capsule around the mesh depending, for example, on the mesh density and pore size. In meshes where the tissue is incorporated into the interstices of the mesh, the fibrous connective tissue forms a strong mechanical link between the mesh and the adjacent tissue. However, the tissue can also force the mesh pore to expand and distort, causing the mesh fabric size to shrink. The extent of the FBR to the non-absorbable mesh generally depends on the amount of synthetic polymer in contact with bodily tissue, with higher density meshes typically triggering a greater FBR than lower density meshes. This greater, chronic FBR that is associated with higher density meshes in turn creates denser, less flexible scar tissue that can correspond to increased procedural complications such as chronic pain. Although a low density, large pore mesh provides for fewer complications and less pain, such a mesh may not have sufficient strength, especially in the first few weeks post implantation and/or may not have adequate handling characteristics for reliable implantation.

Absorbable synthetic mesh materials (e.g., polyglactin) have an initial FBR and scar tissue response that is similar to non-absorbable mesh materials. Such meshes are typically absorbed within six months of implantation leaving behind scar tissue. Interestingly, absorbable meshes do not have good long term outcomes, with evidence suggesting that the scar tissue is not strong enough or does not maintain its strength over time in order to maintain repair.

Biologic graft materials can be subdivided into crosslinked and non-crosslinked materials. Biologic graft materials, like synthetic meshes, trigger inflammation and a FBR. Crosslinking biologic grafts renders the collagen somewhat to enzyme activity and thus resistant to on-going digestion and remodeling of collagen in vivo. Crosslinked biologic graft materials tend to become encapsulated in a fibrous tissue in a manner similar to synthetic graft materials. Non-crosslinked materials exhibit evidence of digestion and remodeling where host collagen is deposited as the graft material is digested.

Biologic grafts materials appear to have lower rates of erosion and dyspareunia than synthetic mesh grafts. However, it is reported that inflammation and FBR associated with biologic grafts (e.g., porcine small intestinal submucosa, fetal bovine dermis, cadaveric human dermis, etc.); especially non-crosslinked biologic grafts, diminish as the graft is degraded and eventually resorbed. As the FBR diminishes, the amount of collagenous tissue in the region diminishes. This is believed to be a key factor for late failures associated with biologic grafts, including grafts used for hernia and pelvic floor repair.

Composite graft-mesh materials have also been developed. Examples include composite implants from American Medical Systems, Inc. (e.g., InteXen® LP® non-chemically crosslinked porcine dermis attached to a polypropylene mesh) and C.R. Bard, Inc. (e.g., Avaulta Plus® Biosynthetic Support System, employing a porous, acellular sheet of crosslinked collagen attached to a polypropylene mesh). In each case, however, the composite material comprises a porous polypropylene mesh. Porous meshes, however, introduce the possibility that the tissue in-growth will cause the mesh pores to expand and distort, resulting in mesh shrinkage, as noted above.

SUMMARY OF THE INVENTION

According to one aspect, the present invention provides composite implants for soft tissue repair. The composite implants comprise (a) a substantially two-dimensional piece of biologic matrix material and (b) one or more non-absorbable synthetic polymeric filaments.

In some embodiments, the filaments are present in the implant in a non-woven, non-knitted configuration.

In other embodiments, the filaments are present in the implant in woven or knitted configuration, albeit with a very large pore size.

Such implants are provided to address late failure associated with biologic graft implants, while at the same time avoiding post-surgical complications associated with non-absorbable synthetic mesh implants.

These and other aspects, as well as various embodiments and advantages of the present invention will become readily apparent to those of ordinary skill in the art upon review of the Detailed Description to follow.

DETAILED DESCRIPTION

Figure 1:
FIG. 1 is a schematic top view of a substantially rectangular composite implant, in accordance with an embodiment of the invention.

According to one aspect, the present invention provides composite implants for soft tissue repair that comprise (a) a substantially two-dimensional piece of biologic matrix material and (b) one or more non-absorbable synthetic polymeric filaments. The filaments may be disposed within the composite implant in various configurations, as discussed in more detail below.

The biologic matrix material is present in the implant to provide initial strength at the site soft tissue repair, for example, during the first several weeks of implantation. The one or more non-absorbable synthetic polymeric filaments (also referred to herein as "filaments", "polymeric filaments" and "synthetic filaments") are present in the implant to stimulate a mild, but ongoing, foreign body response, the purpose of which is to maintain the presence of fibrous collagenous tissue at the soft tissue repair site, thereby providing ongoing strength at the repair site after the biologic matrix material is absorbed by the body. Further, as discussed in more detail below, the synthetic filaments are disposed within the implant in various configurations that are adapted to reduce the potential for graft shrinkage.

Thus, the inventors have developed the implants of the present invention for the purpose of reducing late failure that is associated with biologic graft implants, while at the same time avoiding the post-surgical complications that are associated with synthetic mesh implants.

As noted above, the present invention provides composite implants for soft tissue repair that comprise (a) a substantially two-dimensional piece of biologic matrix material and (b) one or more non-absorbable synthetic polymeric filaments.

As used herein a "substantially two-dimensional" piece of material is one whose length and width are at least 10 times greater than its thickness, for example, whose length and width are each independently 10 to 25 to 50 to 100 or more times its thickness. Examples of such materials include ribbons, sheets, and other more complex sheet-like shapes. In many embodiments, such materials will be able to take on a planar configuration, for example, when placed on a planar surface such as a table top. However, such materials need not be planar. For example, such materials may curve in space (e.g., as a substantially two-dimensional orange peel curves around the inner portion of the orange, etc.).

As defined herein, a "biologic matrix material" is a material that comprises one or more extracellular matrix components. Biologic matrix materials for use herein include crosslinked and non-crosslinked allograft (e.g., human cadaveric) materials, as well as crosslinked and non-crosslinked heterograft (e.g., bovine, porcine, equine, etc.) materials. Specific examples of non-crosslinked biologic matrix materials include mammalian non-crosslinked biologic matrix materials, such as human dermis, human fascia lata, fetal bovine dermis and porcine small intestinal submucosa. Specific examples of crosslinked biologic matrix materials include mammalian crosslinked biologic matrix materials such as crosslinked porcine dermis, crosslinked porcine small intestinal submucosa, crosslinked bovine pericardium, and crosslinked horse pericardium. Such materials are typically acellular. Moreover, they are typically predominantly collagen.

As noted above, in addition to a substantially two-dimensional piece of biologic matrix material, composite implants in accordance with the present invention further include one or more synthetic non-absorbable polymeric filaments (e.g., fibers, fibrils, threads, yarns, etc.). Specific examples of synthetic non-absorbable polymeric filaments include those that comprise one or more of the following: (a) polyolefins, including homopolymers and copolymers of C2-C8 alkenes, for example, polyethylene, polypropylene, etc., (b) fluoropolymers, including homopolymers and copolymers of C2-C8 alkenes in which one or more hydrogen atoms are substituted with fluorine, for example, polytetrafluoroethylene and polyvinylidene fluoride, and (c) polyesters, including, for example, polyethylene terephthalate, among various other non-absorbable polymers.

Filament(s) for the implants of the present invention preferably range in denier from 0.1 d to 250 d (e.g., from 0.1 d to 0.25 d to 0.5 d to 1 d to 2.5 d to 5 d to 10 d to 25 d to 50 d to 100 d to 250 d), more preferably from 5 d to 50 d, among other values.

As noted above, filaments are disposed within the composite implants of the invention in configurations which are adapted to reduce the potential for graft shrinkage (e.g., graft shrinkage associated with tissue incorporation and pore expansion).

In some embodiments, the one or more filaments are provided in a non-woven, non-knitted configuration. Thus, in various embodiments, the one or more filaments are not in the form of a woven or knitted mesh. In some embodiments, the one or more filaments are provided in a configuration which minimizes or eliminates the creation of filament pores. In some embodiments, the one or more filaments are provided in a configuration which contains no crossover points or essentially no crossover points (i.e., the implant may contain a total of less than ten filament crossover points, less than five filament crossover points, or no filament crossover points whatsoever).

For example, FIG. 1 is a schematic top view of a substantially rectangular composite implant 100, in accordance an embodiment of the invention. The composite implant 100 comprises a substantially two-dimensional piece of biologic matrix material 110 (e.g., a ribbon shaped piece, such as may be used as a urethral sling, among other possibilities) and a plurality of non-absorbable synthetic polymeric filaments 120 (six filaments are shown). The filaments 120 are disposed within the composite implant in a parallel configuration. The configuration is thus a non-woven, non-knitted configuration. Also the filaments are oriented to follow load bearing vectors within the implant.

Figure 2:
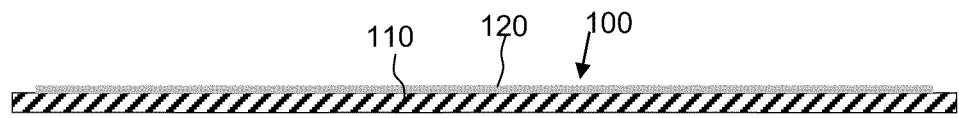
FIGS. 2-4 are possible schematic cross-sectional views of a composite implant like that of FIG. 1, in accordance with various embodiments of the invention.

As elsewhere herein, the filaments 120 of FIG. 1 may be associated with the matrix material 120 in a number of ways. For instance, the filaments 120 may be attached to a surface of the matrix material 120 as shown in schematic cross-section in FIG. 2. The filaments may be attached, for example, by mechanically pressing the filaments into the surface of the matrix material or by adhering the filaments to the matrix material using a suitable biocompatible adhesive, for example, fibrin glue, gelatin or starch, among others.

Figure 3:
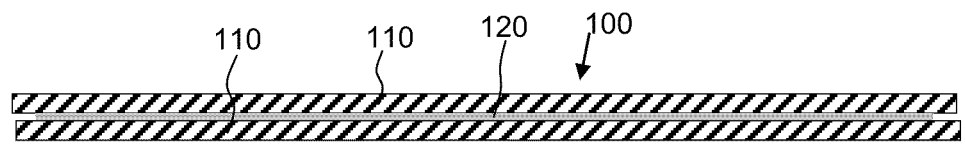

The filaments 120 may be sandwiched between two layers of matrix material 120 as shown in schematic cross-section in FIG. 3. The layers of matrix material may be adhered to one another (and to the filaments) using a suitable adhesive such as one of those listed above.

Figure 4:

The filaments 120 may also be stitched into the layer of matrix material 120 as shown in schematic cross-section in FIG. 4.

Figure 6:
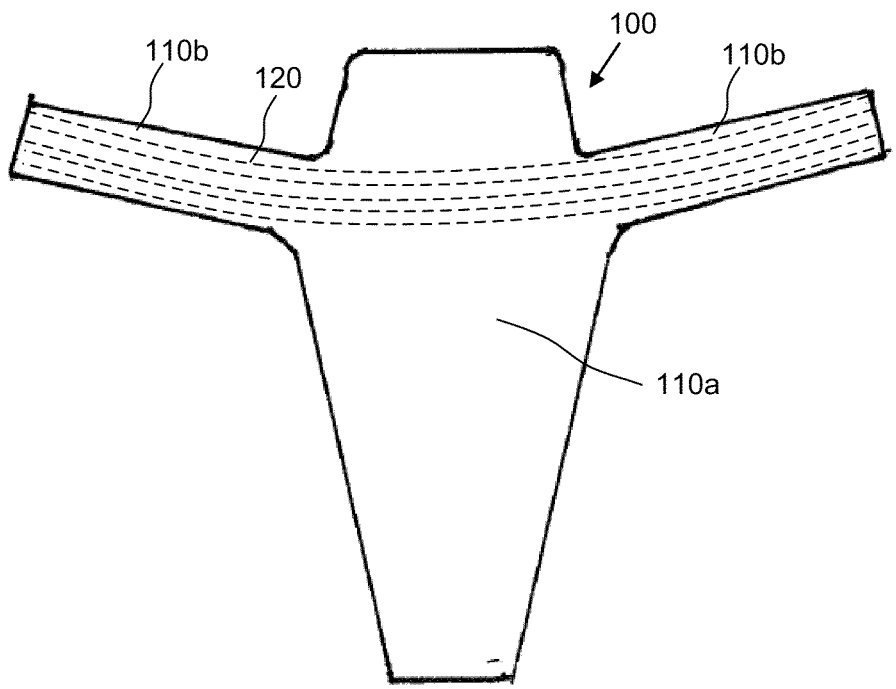
FIGS. 6-9 are schematic top views of composite implants which have a central body portion from which a plurality of arms emanate, in accordance with various embodiments of the invention.

FIG. 6 is a schematic top view of a composite implant 100, in accordance another embodiment of the invention. The composite implant 100 comprises a substantially two-dimensional piece of biologic matrix material 110 and a plurality of non-absorbable synthetic polymeric filaments 120. The biologic matrix material 110 in the embodiment shown includes a central portion 110a and arms 110b. Two arms are shown, but another number of arms (e.g., 3, 4, 5, 6 or more) may be used. Such arms may be useful, for example, in fixating the implant to connective tissues in the body. Moreover, a single arm may be used (e.g., a single arm may be fixated by passing it through a ligament deep in the anatomy, while the central portion may be sutured nearer to the surface of the anatomy).

Each filament 120 in FIG. 6 extends along one arm 110b of the biological matrix material, across the central portion 110a and along the other arm 110b. The filaments 120 are disposed within the composite implant in a substantially parallel configuration. As in FIG. 1, the filament configuration is thus a non-woven, non-knitted configuration that eliminates the creation of filament pores and filament crossover points in the embodiment shown. Also the filaments 120 are oriented to follow load bearing vectors within the implant. In the embodiment shown, the filaments 120 are positioned to stimulate a mild, ongoing foreign body response (in order to maintain the presence of fibrous collagenous tissue) in a band that corresponds to a sub-region of the original implant. The filaments may be, for example, attached to a surface of the matrix material, sandwiched between two layers of matrix material, sewn into the matrix material, and so forth.

Figure 7:
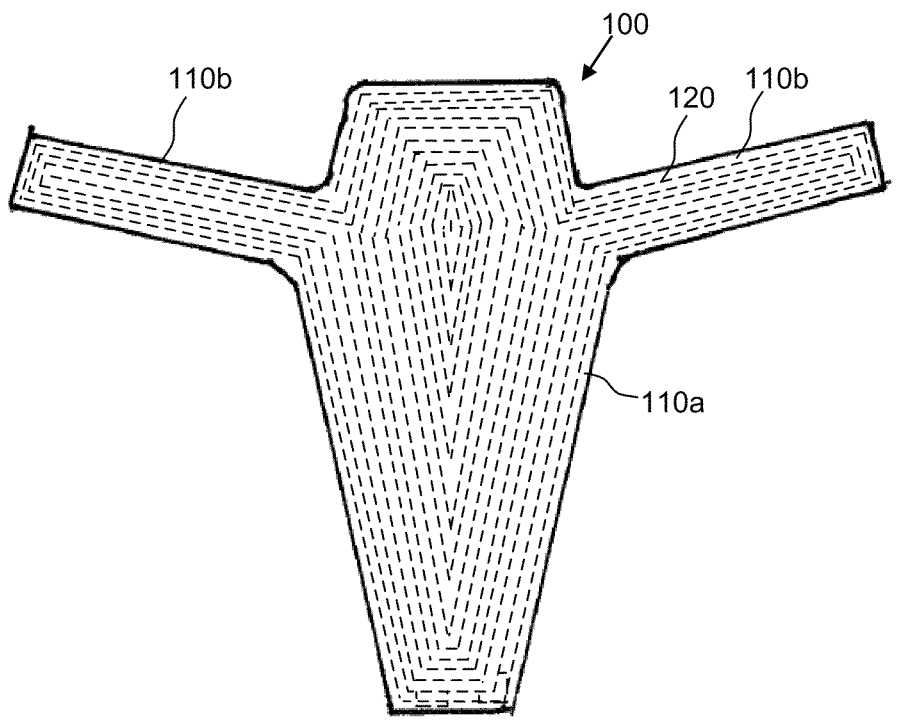

FIG. 7 is a schematic top view of a composite implant 100, in accordance with yet another embodiment of the invention. The composite implant 100 comprises a substantially two-dimensional piece of biologic matrix material 110 and a plurality of non-absorbable synthetic polymeric filaments 120. The biologic matrix material 110 in the embodiment shown is like that of FIG. 6 and includes a central portion 110a and two arms 110b (although another number of arms may be provided). The filaments 120 are disposed within the composite implant in a non-woven, non-knitted configuration that eliminates the creation of filament pores and filament crossover points in the embodiment shown. Unlike FIG. 6, the filaments 120 are present over the entire surface of the implant and thus are adapted to maintain the presence of fibrous collagenous tissue in a region that corresponds approximately to the shape of the original implant. As above, the filaments may be, for example, attached to a surface of the matrix material, sandwiched between two layers of matrix material, sewn into the matrix material, and so forth.

In other embodiments, a plurality of short-length non-absorbable synthetic polymeric filaments is provided for the purpose of reducing late failure that is associated with biologic graft implants, while at the same time reducing the potential for graft shrinkage. Such filaments may be, for instance, less than 50 mm in length, preferably ranging from 1 to 2 to 5 to 7.5 to 10 mm in length.

In such embodiments, the filaments may be without specific orientation and are non-interlocking (although they may overlap). As elsewhere herein, the filaments may be adhered to the biologic matrix material or sandwiched between layers of biologic matrix material, among other possibilities.

For instance, the short-length filaments may be provided in the form of a felt. As a specific example, short-length filaments may be floated as in a wet-laid nonwoven process and attached to a substantially two-dimensional piece of biologic matrix material, for example, using a biocompatible binding agent (e.g., fibrin glue, gelatin, starch, etc.) or pressed into the matrix material, as previously described. The filaments cross over each other in this instance, but lack strength (without the matrix material), due to the relatively short length and lack of interlocks when compared to woven or knit materials. However, the filaments are able to stimulate a mild, but ongoing, foreign body response to maintain the presence of fibrous collagenous tissue at the soft tissue repair site after the biologic matrix material is absorbed by the body.

The density of such short-length filaments may be as high as 40 g/m$^2$ or more in some embodiments, preferably ranging from 5 to 10 to 15 to 20 g/m$^2$, among other possible values.

Figure 5:
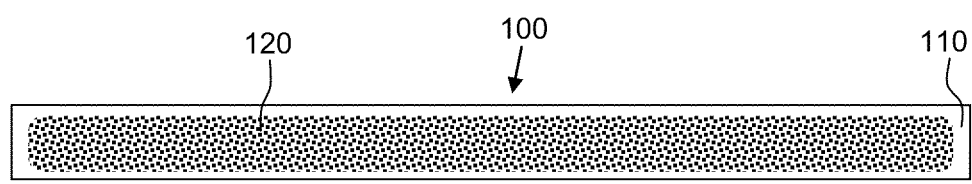
FIG. 5 is a schematic top view of a substantially rectangular composite implant, in accordance with another embodiment of the invention.

FIG. 5 is a schematic top view of a substantially rectangular composite implant 100, in accordance an embodiment of the invention. The composite implant 100 comprises a substantially two-dimensional piece of biologic matrix material 110 (specifically a ribbon shaped piece, such as a sling) and a plurality of short lengths of non-absorbable synthetic polymeric filaments 120 provided in a relatively high density (e.g., a felt of short-length polymeric filaments, etc.). The filaments may be, for example, attached to a surface of the matrix material, sandwiched between two layers of matrix material, and so forth.

Figure 8:
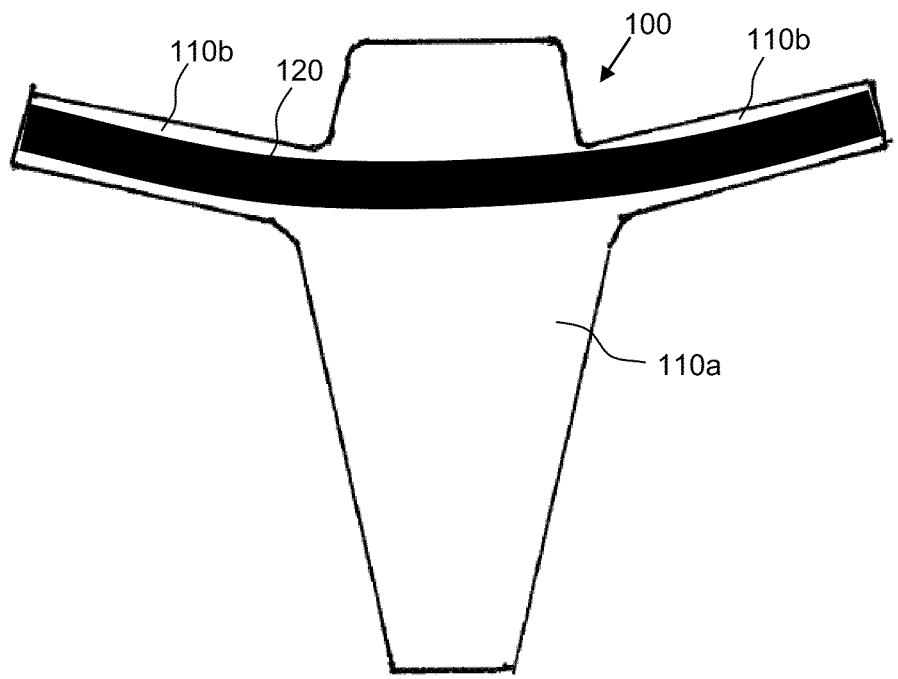

FIG. 8 is a schematic top view of a composite implant 100, in accordance another embodiment of the invention. The composite implant 100 comprises a substantially two-dimensional piece of biologic matrix material 110 and a plurality of short lengths of non-absorbable synthetic polymeric filaments 120 provided in a relatively high density (e.g., a felt of short-length polymeric filaments, etc.). The substantially two-dimensional piece of biologic matrix material 110 in the particular embodiment shown includes a central portion 110a and two arms 110b. The filaments 120 are grouped in the form of a band that extends along one arm 110b of the biological matrix material, across the central portion 110a and along the other arm 110b. The band of filaments 120 is oriented to follow load bearing vectors within the implant. In the embodiment shown, the filaments 120 are positioned to stimulate a mild, ongoing foreign body response in a band that corresponds to a sub-region of the original implant. As elsewhere, the filaments may be, for example, attached to a surface of the matrix material, sandwiched between two layers of matrix material, and so forth.

Figure 9:
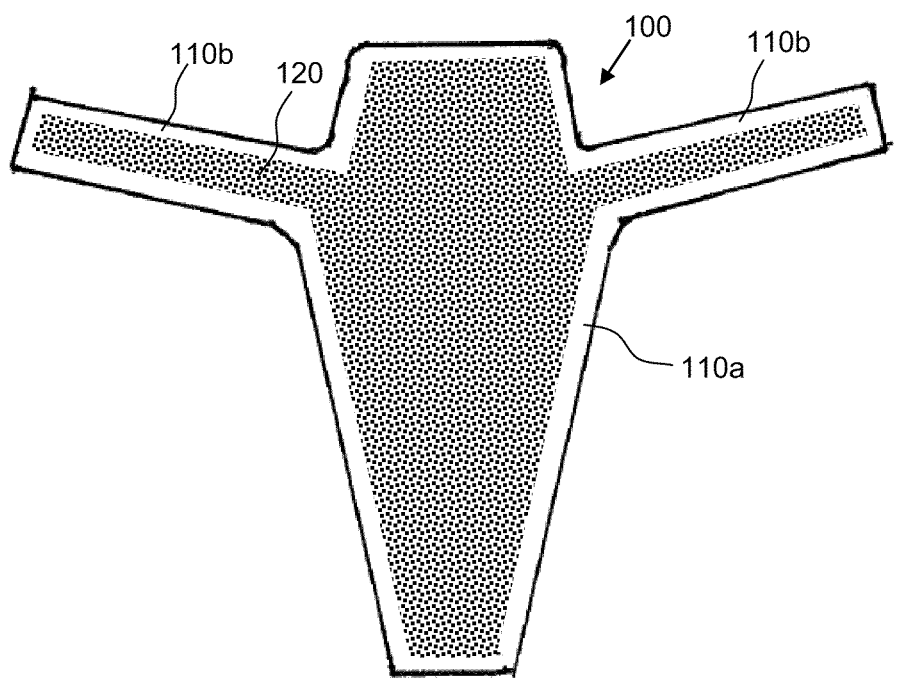

FIG. 9 is like FIG. 8, except that short-length non-absorbable synthetic polymeric filaments 120 (e.g., a felt of short-length polymeric filaments, etc.) are present over the entire surface of the implant in relatively high density and thus are adapted to maintain the presence of fibrous collagenous tissue in a region that corresponds approximately to the shape of the original implant.

As noted above, in some embodiments, the non-absorbable synthetic polymeric filaments are provided in a woven or knitted configuration, albeit with a very large pore size. For example, the pore size in certain embodiments may be at least 1 cm, preferably ranging from 1 to 2 to 3 to 4 to 5 cm. The density may range, for example, from 5 to 10 to 15 to 20 g/m$^2$, among other possible values.

Due to the large pore size and low density, such a woven or knitted filamentous material may not have sufficient initial strength on its own. However, by combining the filamentous material with the matrix material, strength is adequate. Moreover, the filamentous material is able to stimulate a mild, but ongoing, foreign body response, to maintain the presence of fibrous collagenous tissue at the soft tissue repair site after the biologic matrix material is absorbed by the body.

As above, such a woven or knitted filamentous material may be, for example, attached to a surface of the matrix material, sandwiched between two layers of matrix material, sewn into the matrix material, and so forth. Such a woven or knitted filamentous material may, for example, correspond substantially to the shape of the matrix material (e.g., as shown in FIGS. 5 and 9). Alternatively, such a woven or knitted filamentous material may, for example, correspond to only a portion of the matrix material. For example, the woven or knitted filamentous material may be provided in the form of a band as shown in FIG. 8. In this way, the band of woven or knitted filamentous material may be oriented to follow load bearing vectors within the implant.

In certain embodiments, the composite implants of the invention comprise one or more agents in addition to the biologic matrix material and non-absorbable synthetic polymeric filament(s). Examples of such additional agents include agents that promote tissue response, analgesic agents, anesthetic agents, antibiotic agents, and antimicrobial agents, among others.

The additional agents may be associated with the composite implants in various ways, including the following, among others: (a) loaded into the interior (bulk) of the filament(s) and/or matrix material, (b) bound to the surface of the filament(s) and/or matrix material by covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (c) applied as a coating (biostable or biodegradable) that at least partially surrounds the filament(s) and/or matrix material, and (d) combinations of the forgoing.

Agents that promote tissue response (and thus tissue integration) include agents which, like the synthetic filaments of the invention, promote growth of collagenous tissue. Examples of such materials include certain biodegradable polymers, for instance, biodegradable polyesters such as polylactide (PLA), polyglycolide (PLG), and poly(lactide-co-glycolide) (PLGA), among many others, which produce inflammation as they degrade due to pro-inflammatory breakdown products, leading to the formation of collagenous tissue such as scar tissue. The rate and degree of biodisintegrable polymer breakdown can depend upon a number of factors including monomer content (e.g., choice of monomer or ratio of monomers, if a copolymer), degree of crystallinity, polymer architecture, exposed surface area, and so forth. Other polymers include alginate, chitin, hyaluronic acid, collagen, and proteins that promote a tissue inflammatory response, thereby promoting healing and tissue integration. Further specific examples of materials that promote collagenous tissue growth may be selected, for instance, from growth factors (e.g., transforming growth factor beta (TGF-beta), epidermal growth factor (EGF), platelet-derived growth factor (PDGF), insulin-like growth factor (IGF), basic fibroblast growth factor (bFGF), vascular endothelial growth factor (VEGF), etc.) and other materials such as cytokines (i.e., substances made by cells that are used by the same, or other cells, to produce some type of response), endotoxins, chemokines, prostaglandins, lipid mediators and other mitogens, various natural and synthetic proinflammatory agents, sclerosing agents, cells, including stem cells and other suitable cells derived from the host patient, including fibroblast, myoblast and/or other progenitor cells, among other materials. See, e.g., Pub. No. US2006/0205998 and the references cited therein.

Various aspects of the invention of the invention relating to the above are enumerated in the following paragraphs:

Aspect 1. A composite implant for soft tissue repair comprising: (a) a substantially two-dimensional piece of biologic matrix material and (b) one or more non-absorbable synthetic polymeric filaments, the filaments being present in the implant in a non-woven, non-knitted configuration.

Aspect 2. The composite implant of aspect 1, wherein the biologic matrix material is a non-crosslinked biologic matrix material.

Aspect 3. The composite implant of aspect 1, wherein the biologic matrix material comprises non-crosslinked mammalian dermis.

Aspect 4. The composite implant of aspect 1, wherein the biologic matrix material comprises non-crosslinked fetal bovine dermis.

Aspect 5. The composite implant of aspect 1, wherein the biologic matrix material is in the form of an elongated strip.

Aspect 6. The composite implant of aspect 1, wherein the biologic matrix material comprises a central body portion and one or more arms extending from the central body portion.

Aspect 7. The composite implant of aspect 1, wherein the one or more non-absorbable synthetic polymeric filaments comprise a polyolefin.

Aspect 8. The composite implant of aspect 1, wherein the one or more non-absorbable synthetic polymeric filaments comprise polypropylene.

Aspect 9. The composite implant of aspect 1, wherein the one or more non-absorbable synthetic polymeric filaments range in denier from 5 d to 50 d.

Aspect 10. The composite implant of aspect 1, wherein the one or more non-absorbable synthetic polymeric filaments are adhered to the biologic matrix material.

Aspect 11. The composite implant of aspect 1, wherein the one or more non-absorbable synthetic polymeric filaments are sandwiched between two of the pieces of biologic matrix material.

Aspect 12. The composite implant of aspect 1, wherein the one or more non-absorbable synthetic polymeric filaments are stitched into the biologic matrix material.

Aspect 13. The composite implant of aspect 1, comprising a plurality of non-absorbable synthetic polymeric filaments.

Aspect 14. The composite implant of aspect 13, wherein the non-absorbable synthetic polymeric filaments do not cross one another.

Aspect 15. The composite implant of aspect 14, wherein the non-absorbable synthetic polymeric filaments are substantially parallel with one another.

Aspect 16. The composite implant of aspect 1, wherein the biologic matrix material comprises a central body portion and first and second arms extending from the central body portion, and wherein a plurality of substantially parallel non-absorbable synthetic polymeric filaments extend along the first arm, across the central body portion and along the second arm.

Aspect 17. The composite implant of aspect 13, wherein the non-absorbable synthetic polymeric filaments do not form pores.

Aspect 18. The composite implant of aspect 13, wherein the non-absorbable synthetic polymeric filaments are short filaments that range from 1 to 10 mm in length.

Aspect 19. The composite implant of aspect 18, wherein the biologic matrix material comprises a central body portion and first and second arms extending from the central body portion, and wherein a band of the non-absorbable synthetic polymeric filaments extends along the first arm, across the central body portion and along the second arm.

Aspect 20. The composite implant of aspect 18, wherein the non-absorbable synthetic polymeric filaments are present in a density of ranging from 5 to 20 g/m$^2$ over at least a portion of the implant.

Aspect 21. A composite implant for soft tissue repair comprising: (a) a substantially two-dimensional piece of biologic matrix material and (b) one or more non-absorbable synthetic polymeric filaments, the filaments being present in the implant in a woven or knitted configuration wherein the pore size ranges from 1 to 5 cm and the filament density ranges from 5 to 20 g/m$^2$ over at least a portion of the implant.

Although various embodiments are specifically illustrated and described herein, it will be appreciated that modifications and variations of the present invention are covered by the above teachings and are within the purview of any appended claims without departing from the spirit and intended scope of the invention. For instance, although non-absorbable synthetic polymeric filaments are describe above, the implants of the invention are configured to create an ongoing foreign body response in the region of the implant in order to maintain the presence of fibrous collagen in the region of the implant after the biologic matrix material is resorbed. Therefore, it should be understood that other non-absorbable synthetic materials may be introduced into the implant as well.

The invention claimed is:

1. A composite implant for soft tissue repair comprising: (a) a substantially two-dimensional piece of biologic matrix material and (b) a plurality of non-absorbable synthetic polymeric filaments less than 50 mm in length, the filaments being present in the composite implant in a form of a felt band corresponding to a sub-region of the composite implant, wherein the biologic matrix material comprises a central body portion and first and second arms extending from the central body portion, and wherein said band extends along the first arm, across the central body portion and along the second arm.

2. The composite implant of claim 1, wherein the biologic matrix material is a non-crosslinked biologic matrix material.

3. The composite implant of claim 1, wherein the biologic matrix material comprises non-crosslinked mammalian dermis.

4. The composite implant of claim 1, wherein the biologic matrix material comprises non-crosslinked fetal bovine dermis.

5. The composite implant of claim 1, wherein the non-absorbable synthetic polymeric filaments comprise a polyolefin.

6. The composite implant of claim 1, wherein the non-absorbable synthetic polymeric filaments comprise polypropylene.

7. The composite implant of claim 1, wherein the non-absorbable synthetic polymeric filaments range in denier from 5 d to 50 d.

8. The composite implant of claim 1, wherein the non-absorbable synthetic polymeric filaments are adhered to the biologic matrix material.

9. The composite implant of claim 1, wherein the non-absorbable synthetic polymeric filaments are sandwiched between two pieces of biologic matrix material.

10. The composite implant of claim 1, wherein the non-absorbable synthetic polymeric filaments are stitched into the biologic matrix material.

11. The composite implant of claim 1, wherein the non-absorbable synthetic polymeric filaments comprise short filaments that range from 1 to 10 mm in length.

12. The composite implant of claim 11, wherein the non-absorbable synthetic polymeric filaments are present in a density of ranging from 5 to 20 $g/m^2$ over at least a portion of the composite implant.

13. The composite implant of claim 1, wherein the felt band is formed by a wet-laid process.

14. The composite implant of claim 1, wherein a width of the felt band in the central body portion is less than or equal to a width of the felt band extending along the first and second arms.

15. The composite implant of claim 1, wherein an area of the central body portion crossed by the felt band constitutes only a portion of a total area of the central body portion.

* * * * *